(12) United States Patent
Martinerie et al.

(10) Patent No.: US 7,697,979 B2
(45) Date of Patent: Apr. 13, 2010

(54) ANALYSIS METHOD AND REAL TIME MEDICAL OR COGNITIVE MONITORING DEVICE BASED ON THE ANALYSIS OF A SUBJECT'S CEREBRAL ELECTROMAGNETIC ACTIVITY USE OF SAID METHOD FOR CHARACTERIZING AND DIFFERENTIATING PHYSIOLOGICAL OR PATHOLOGICAL STATES

(75) Inventors: Jacques Martinerie, Palaiseau (FR);
Michel Le Van Quyen, Paris (FR);
Jean-Philippe Lachaux, Bourg-la-Reine (FR); Bernard Renault, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 1340 days.

(21) Appl. No.: 10/531,311

(22) PCT Filed: Oct. 14, 2003

(86) PCT No.: PCT/FR03/50090
§ 371 (c)(1),
(2), (4) Date: Apr. 13, 2005

(87) PCT Pub. No.: WO2004/035130
PCT Pub. Date: Apr. 29, 2004

(65) Prior Publication Data
US 2006/0015034 A1    Jan. 19, 2006

(30) Foreign Application Priority Data
Oct. 18, 2002    (FR) .................................. 02 13007

(51) Int. Cl.
*A61B 5/04* (2006.01)
(52) U.S. Cl. .................................................. 600/544
(58) Field of Classification Search ................. 600/544, 600/545
See application file for complete search history.

(56) References Cited

U.S. PATENT DOCUMENTS 4,201,224 A    5/1980    John (Continued)

FOREIGN PATENT DOCUMENTS

WO    00/10455    3/2000

(Continued)

OTHER PUBLICATIONS

Lachaux et al.: "Measuring Phase Synchrony in Brain Signals" Human Brain Mapping, vol. 8, pp. 194-208, 1999. XP002247405.

(Continued)

*Primary Examiner*—Charles A Marmor, II
*Assistant Examiner*—Christian Y Jang
(74) *Attorney, Agent, or Firm*—Oblon, Spivak, McClelland, Maier & Neustadt, L.L.P.

(57) ABSTRACT

A method for analyzing synchronizations of the electroencephalography of an individual using a set of sensors starting from cerebral electromagnetic analysis of the individual. The method creates a database by acquisition and digitization of electrophysiological signals output from the sensors, and calculates the degree of synchronization existing between all pairs of sensors recorded in an assembly protocol, in frequency bands between 0 and 2000 Hz, to build up the database of classes each characterizing a reference state. The method further performs statistical validation of a period analyzed in real time, which assigns this period to a class in the database, and detects a specific period with a determined degree of synchronization. A device implements this method.

18 Claims, 6 Drawing Sheets

U.S. PATENT DOCUMENTS

| | | | |
|---|---|---|---|
| 4,846,190 | A | 7/1989 | John |
| 6,304,775 | B1 | 10/2001 | Sackellares et al. |
| 2001/0044573 | A1* | 11/2001 | Manoli et al. ............... 600/383 |
| 2002/0042563 | A1 | 4/2002 | Borsook et al. |
| 2003/0004428 | A1* | 1/2003 | Pless et al. .................. 600/544 |
| 2004/0059241 | A1* | 3/2004 | Suffin ......................... 600/544 |

FOREIGN PATENT DOCUMENTS

WO           01/37724         5/2001

OTHER PUBLICATIONS

Quiroga R Q et al: "Event synchronization: a simple and fast method to measure synchronicity and time delay patterns" Physical Review E (Statistical, Nonlinear, and Soft Matter Physics), vol. 66, No. 4, pp. 41904-41909, Oct. 2002. XP002247968.

Le Van Quyen M et al: "Comparison of Hilbert transform and wavelet methods for the analysis of neuronal synchrony" Journal of Neuroscience Methods, vol. 111, No. 2, pp. 83-98, Oct. 30, 2001. XP002248012.

J.-P. Lachaux et al. "Study single-trials of phase synchronous activity in the brain," International Journel of Bifurcations and Chaos, vol. 10 No. 10 (2000) pp. 2429-2439.

M. Le Van Quyen et al. "Anticipation of epileptic seizures from standard EEG recordings," The Lancet, vol. 357, Jan. 20, 2001, pp. 183-188.

J. Martinerie et al. "Epileptic seizures can be anticipated by non-linear analysis," Nature Medicine, vol. 4, No. 10, Oct. 1998, pp. 1173-1176.

F. Varela et al. "The Brainweb: phase synchronization and large-scale integration," Nature Reviews- Neurosciences, vol. 2, Apr. 2001, pp. 229-239.

* cited by examiner

ANALYSIS METHOD AND REAL TIME MEDICAL OR COGNITIVE MONITORING DEVICE BASED ON THE ANALYSIS OF A SUBJECT'S CEREBRAL ELECTROMAGNETIC ACTIVITY USE OF SAID METHOD FOR CHARACTERIZING AND DIFFERENTIATING PHYSIOLOGICAL OR PATHOLOGICAL STATES

TECHNICAL DOMAIN

This invention relates to an analysis method and a device for real time medical or cognitive monitoring using the analysis of the cerebral electromagnetic activity of an individual, with applications of this method for differentiation and characterisation of physiological and pathological states, particularly for real time processing of anticipation of epilepsy seizures.

STATE OF PRIOR ART

Role of Cerebral Interactions in Man: Dynamic Mapping

Any cerebral action is the result of a cooperation between several spatially distributed neuron networks. At the present time, and despite recent progress, the principal cerebral imaging techniques, namely EEG (electroencephalography), MEG (magnetoencephalography), FMRI (functional magnetic resonance imaging) and PET (positron emission tomography), only provide a map of cerebral activations without directly reporting interactions between these activations. Characterisation of these functional networks requires:

identification of the cerebral regions involved;
understanding of interaction mechanisms between them; and
precise quantification of these interactions.

It is impossible to observe operation of these networks simply from a map of cerebral activities. How would it be possible to decide which zones among all active zones at any one time participate in a particular network? A simple observation that two zones are active at the same time is not enough to conclude that they are engaged in the same pathological or cognitive process. To elucidate these exchange mechanisms, it is necessary to have explicit assumptions about the nature of these links and to have technical means of observing them.

All approaches known in prior art are based on the idea that the existence of a coupling between two zones must result in a correlation between their activities. However, the activity of a group of neurons, for example a cortical column, can be characterised by two measurement types:

time coding with the rate of neuron discharges per second; or
coding by synchronisation of oscillatory activities of cerebral zones involved in the same network.

The purpose of the invention is to propose a method for dynamic mapping of the brain starting from such a phase synchronism measurement, starting from the assumption according to which dynamic links between neuron groups occur by synchronisation of oscillatory activities in some frequency bands between 0 and 2000 Hz.

Example Application to Pathology: Anticipation of Epilepsy Seizures

In the remainder of the description, the method according to the invention is described with reference to medical monitoring of a patient for anticipation of epilepsy seizures in real time, simply as an example and to make the description clearer. Obviously, it would be possible to apply the method according to the invention to other fields and to characterise and then recognise physiological or pathological states by changing the database.

Epilepsy is one of the most frequent neurological complaints in children and adults (1% of the population), and is the result of neuron disorder expressed by recurrent paroxysmal or paroxystic discharges of the cerebral cortex. The clinical result of epilepsy is the sudden occurrence of the symptoms of a seizure. This sudden emergence is difficult to interpret as a response to a triggering external factor, which is not present in most situations, except for the rare reflex epilepsies. The transition between an "intercritical" state and the critical state (the seizure) is one of the primordial phenomenologies of epilepsy and this intermittence appears to be an unpredictable product of an internal self-organization of the brain.

No traditional method (linear analysis) has yet been able to significantly anticipate this state of seizure.

Two recent publications, references [1] and [2] at the end of the description, describe a process that under some conditions can make it possible to anticipate seizures lasting several minutes using new strategies output from the theory of dynamic systems. Non-linear dynamic methods are derived from known mathematics under the generic term "Chaos theory". They show how there can be precise laws or determinisms behind an apparently random electroencephalographic signal. The possibility of anticipating the occurrence of seizures opens up very broad prospects.

Anticipation of seizures would be useful for the large number of patients with a drug resistant epilepsy, which accounts for about 25% of all epileptic patients. The intermittent and unexpected occurrence of seizures is a recognised factor of mortality (by car accidents or sudden death) and morbidity (particularly brain and face traumatisms). Furthermore, patients consider the unpredictable nature of seizures to be one of the most important factors affecting their poor life quality. Limitations related to the risk of seizures are social (isolation due to the fear of a seizure in public), professional (risk activities that epileptics cannot perform) and personal (car driving prohibited). The possibility of anticipating the occurrence of seizures would be a means of helping epileptics to live better with their seizures. In addition to the possibility of alerting the patient about the imminence of a seizure, anticipation strategies should also be helpful for making complementary examinations for the purposes of a pre-surgical checkup of their epilepsy. Furthermore, such strategies should open up the opportunity for therapeutic actions before the seizure has time to emerge.

Document reference [1] mentioned above is based on quantification of the similarity between a "normal" reference dynamic and the emerging epileptic dynamic. This similarity index is calculated independently for each recorded channel. The space and time components of cerebral changes can be obtained by aligning changes in the statistical deviation of the indexes of each channel. Nevertheless, this method only indirectly takes account of the spatial aspect of modifications to electroencephalography variations (intracranial and surface) that we use to predict the imminence of a seizure. However, strong evidence suggests that this period reflects the transition from a disordered state to a more ordered (or less complex) state that would very likely correspond to changes in the synchronisation of several neuron assemblies distributed in different cerebral structures. The ideal method of increasing the efficiency of anticipation would be to have additional information about the space-time behaviours of epileptogenic variations such as subtle variations in activity or interdependences between distant cerebral regions. Many observations suggest that it is often very difficult to determine a single zone of epileptic malfunctions as being the origin of a seizure. In particular, recent work has very much suggested the importance of imagining partial epilepsies as being a manifestation of a networked structure. It is quite probable that propagation of the discharge facilitates a number of connections between multiple neuron assemblies, thus more efficiently modifying local and remote neuron connections. Thus, the organization of epileptic malfunctions can no longer be envisaged statically or as a local malfunction (circumscribed epileptic focus), but rather satisfies a complex dynamic space-time model that spatially involves neuron networks connected by abnormally facilitated connections involving some synchronised behaviours in time.

Linear techniques (cross-correlations in the time domain or consistencies in the frequency domain) have frequently been used in the past to study the spatial organization of the epileptogenic network and to characterise interactions between the epileptogenic network and the remainder of the brain. In the case of an analysis between macroscopic signals, these methods are often limited by assumptions made in them related to the stationarity of signals and the linear nature of interactions. This is particularly problematic because non-linear behaviour is significantly increased in an epileptic period.

The purpose of this invention is to overcome these limitations.

PRESENTATION OF THE INVENTION

The invention relates to a method for analysing synchronisations of the electroencephalography of an individual using a set of sensors starting from the cerebral electromagnetic analysis of the patient, characterised in that it comprises the following steps consisting of:

a step to create a database comprising:
  a phase for acquisition and digitisation of electrophysiological signals output from these sensors,
  a phase to calculate the degree of synchronisation existing between all pairs of sensors recorded in an assembly protocol, in frequency bands between 0 and 2000 Hz, to build up this database of classes each characterising a reference state;
a step for statistical validation of a period analysed in real time, which assigns this period to a class in the database,
a step to detect a specific period with a determined degree of synchronisation.

Advantageously, the said method includes an analysis associated with at least one type of electrophysiological signals among electrocardiograms, electrooculograms, electrodermograms, breathing signals.

Advantageously, a PLS method is used during the statistical validation step, which estimates the phase difference between oscillations of signals from two electrodes. The statistical level of the PLS synchronisation between two signals is evaluated using the circular variance of the phase difference between the signals or using the normalised Shannon entropy of the phase difference between the signals.

The method according to the invention can be used to characterise and differentiate between physiological or pathological states, for example for anticipation of epilepsy seizures.

The method according to the invention can be used in other application fields, such as:

sleep: differentiation between different sleep stages;

anaesthesia: characterisation of stages of falling asleep under anaesthesia with automatic control of regulation of the injected substance;

depression: with electrophysiological monitoring of a depressive patient and characterisation of his traits or states and consequently adjustment of his treatment;

schizophrenia: with electrophysiological monitoring of a patient and quantification of his traits or states for diagnosis assistance and therapeutic purposes;

diagnosis assistance for neurological diseases such as Parkinson's and Alzheimer's diseases;

characterisation of cognitive states (levels of vigilance and attention, perception and conscious and unconscious recognition of visual, auditory, somesthetic and emotional stimulations (fear, joy, etc.).

The invention also relates to a real time medical or cognitive monitoring device starting from the cerebral electromagnetic analysis of an individual, characterised in that it comprises:

means of acquiring and digitising electrophysiological signals output from sensors;

means of calculating the synchronisation between all pairs of sensors recorded in an assembly process, in frequency bands between 0 and 2000 Hz, to build up a database of classes each characterising a reference state;

means of statistical validation of a period analysed in real time to assign this period to a class in the database;

means of detecting a cognitive period or a specific pathological period;

means of sending an alert signal if applicable.

Advantageously, the device according to the invention is a standalone, lightweight device that the patient can carry himself or herself. The device according to the invention may be miniaturised so that it can be implanted subcutaneously like a stimulator, so that patients can be completely autonomous.

DETAILED PRESENTATION OF PARTICULAR EMBODIMENTS

Neuroelectric activity in a restricted frequency band is characterised by its energy and its phase, such that demonstration of a relation between two groups of neurons within a given frequency band requires the demonstration of a significant correlation between variations in the energy or phase of each. The most frequently used method at the moment makes simultaneous use of the energy and the phase. It consists of calculating consistency between signals using the "Magnitude Squared Coherence" (MSC) index.

This MSC index is a global measurement in which it is difficult to separate the influence of the phase from the influence of energy. A correlation between variations of the phases of the two signals may be sufficient to demonstrate coupling between two neuron groups (document reference [3]).

The method according to the invention enables a measurement of the synchronism, using the phase only, namely the "Phase Locking Statistics" (PLS) method. For a given latency, this method estimates the phase difference between oscillations of signals from two electrodes. If this phase difference is relatively constant during the analysed period, a high PLS index will be obtained which is a sign that the two electrodes are significantly synchronous.

This PLS method is sufficiently precise to detect periods with synchronism and is therefore suitable to describe a series of transient synchronisms like those presumed to occur in cognitive processing or to characterise more sustained synchronisms like those presumed to characterise pathological states.

This method can be used to measure the degree of synchronisation between the activities of various cerebral regions. Synchronism between two neuron groups is defined within a given frequency band as being a significant correlation between variations in their phase with time; this is called "phase-locking". Nevertheless, considering volume effects (the activity of a single neuron population can thus be picked up by two relatively remote electrodes) and neuron background noise, the only way to detect synchronism between two regions is to use a statistical approach. The statistical validity of the measurements is then tested by the construction of bi-varied surrogate data.

The invention can thus use a statistical estimating method based on the use of surrogate data, which the PLS method uses to apply itself to non-stationary neuroelectric signals (unlike the MSC method), as is the case for most biological signals.

Therefore the method according to the invention is a real time medical or cognitive monitoring process based on an analysis of the cerebral electromagnetic activity of an individual associated with analysis of any other electrophysiological signals (electrocardiograms electrooculograms, electrodermograms, breathing signals), particularly to detect specific cognitive or pathological periods, for example an epilepsy seizure under preparation, and to provide an alert signal in all cases necessary to enable prevention or a therapeutic action.

Figure 1:
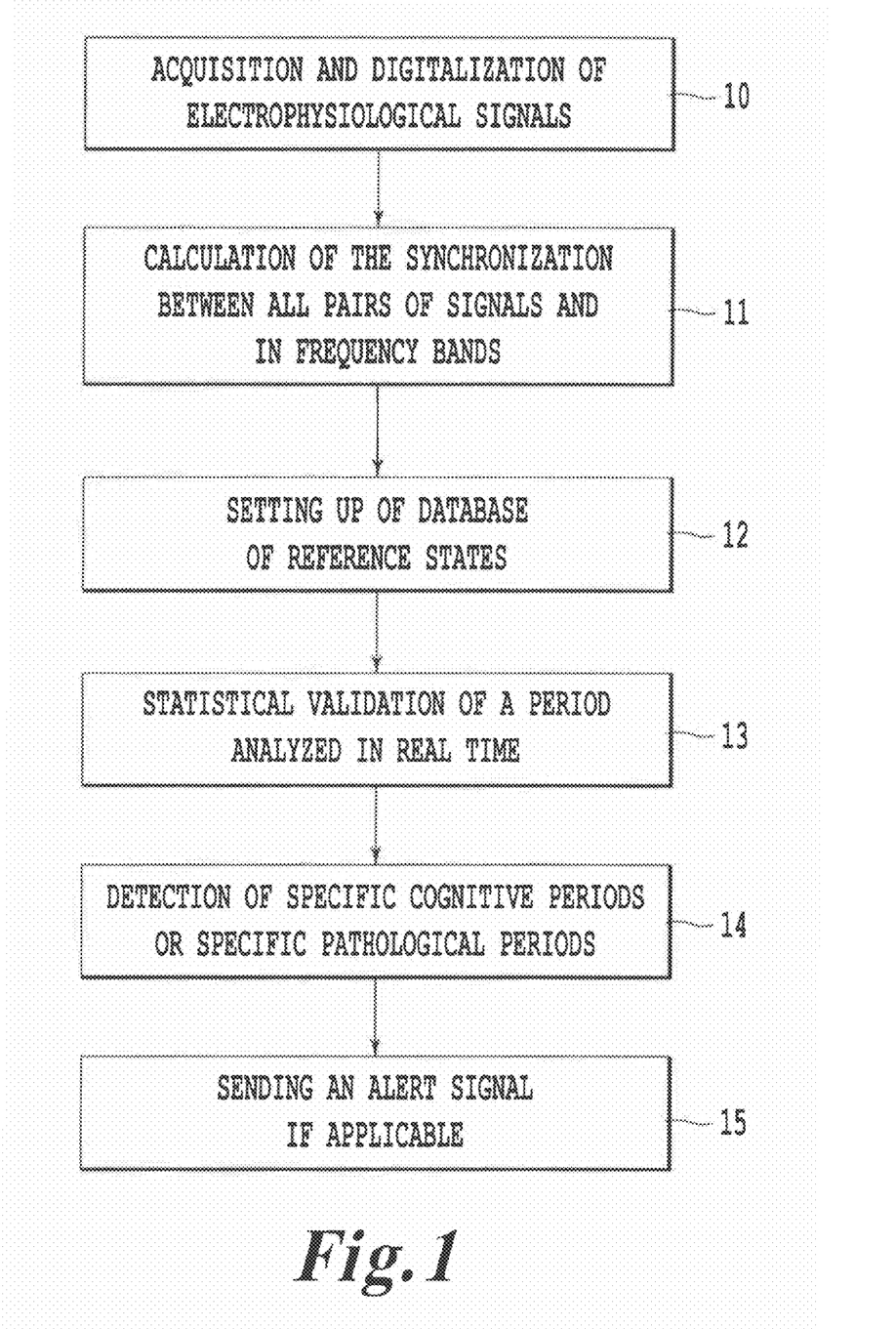
FIG. 1 illustrates the different steps in the method according to the invention, starting from the electroencephalogram (EEG) analysis.

As illustrated in FIG. 1, the process according to the invention includes the following steps:
- an electrophysiological signals acquisition and digitisation step 10: in general, a headset placed on an individual's scalp and provided with 27 to 128 electrodes depending on the problem to be solved, can be used to record the individual's cerebral activity with a fairly good spatial resolution. Some additional signals may be acquired at the same time (eye movement signal, heart activity signal, etc.);
- a step 11 to calculate synchronisation between all pairs of signals and in several frequency bands to build up a database (step 12) of reference states depending on the selected problematics (pathological, sleep, wake, vigilance, etc.);
- a step 13 for statistical validation of the period analysed in real time, to classify this period starting from the database. This validation is based on a non-parametric multidimensional discrimination method;
- a step 14 to detect specific cognitive or pathological periods;
- a step 15 for sending an alert signal, if applicable.

Figure 2:
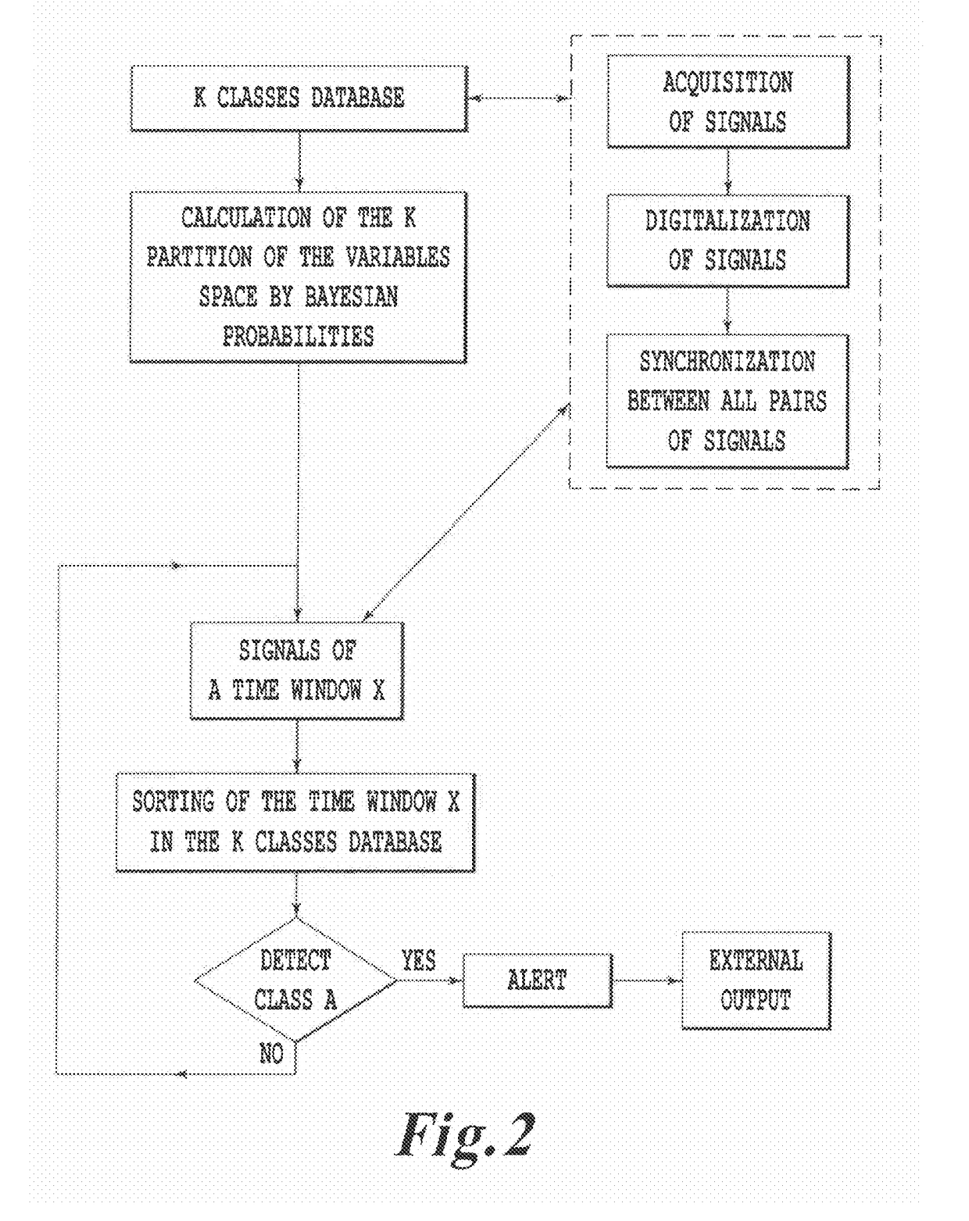
FIG. 2 illustrates the steps in the method according to the invention more precisely.

More precisely, the following steps can be performed in sequence starting from a database with k classes, as illustrated in FIG. 2:
- calculate the partition of the variables space by Bayesian probabilities $S_{ref}^{k}$;
- sort a time window x, for example lasting for 10 seconds, in the base of k classes;
- detect a class with alert if applicable.

Figure 3A:
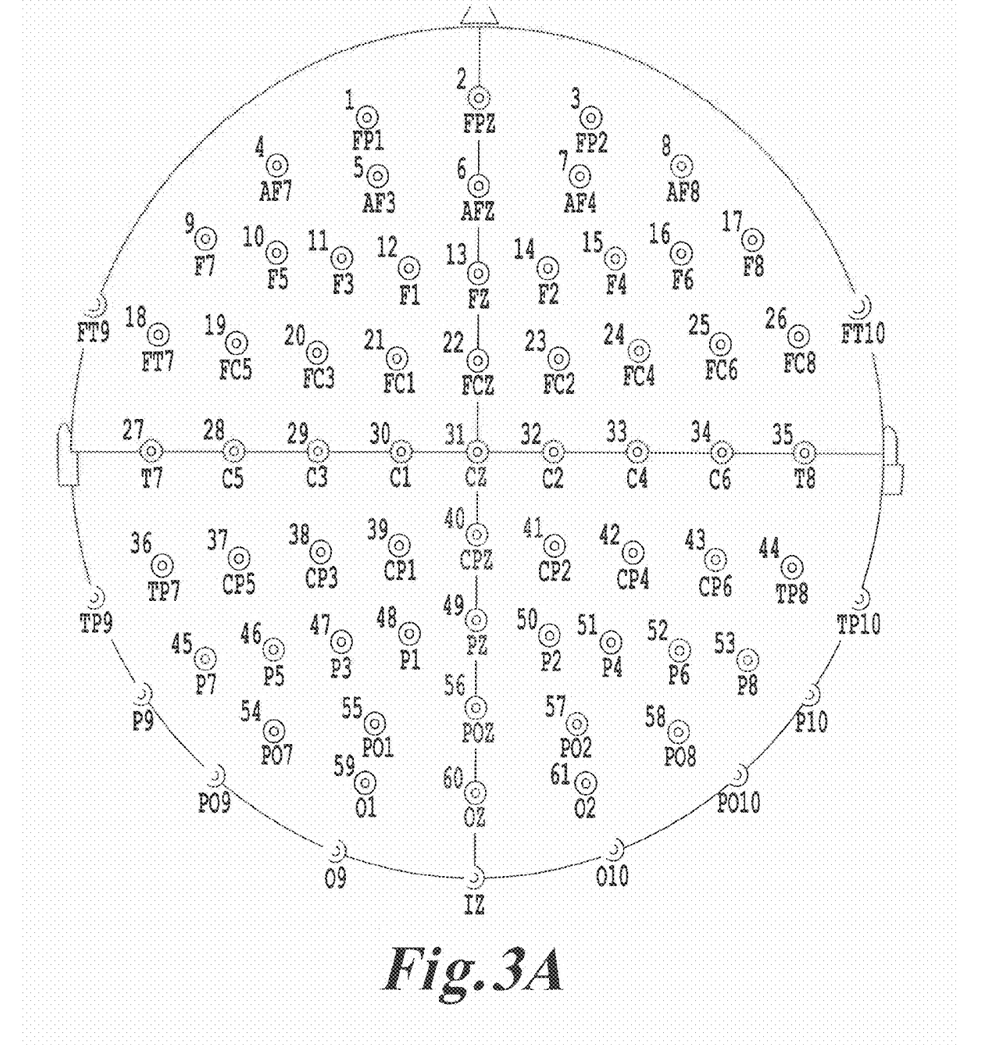
FIGS. 3A and 3B illustrate the device according to the invention.
Figure 3B:
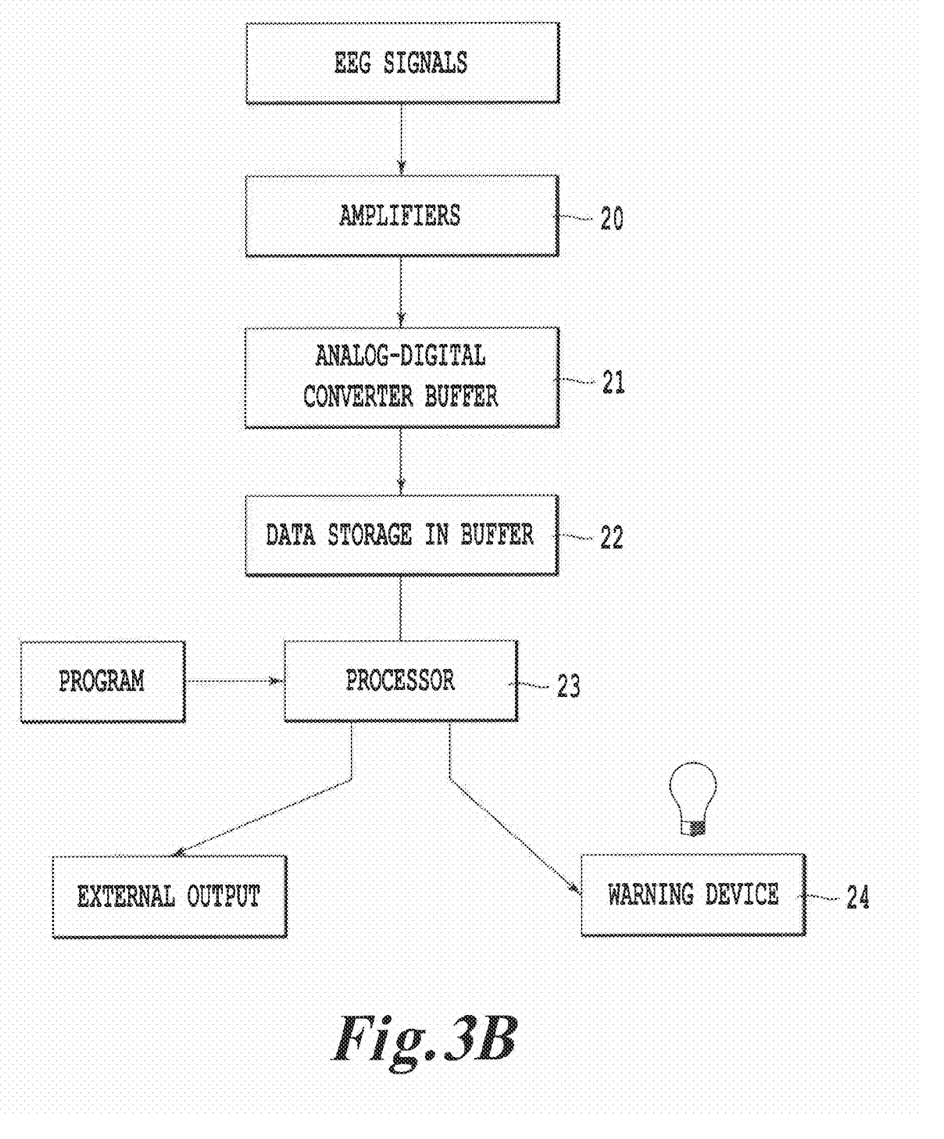

As illustrated in FIGS. 3A and 3B, the independent real time medical or cognitive monitoring device using an electromagnetic cerebral analysis of an individual includes circuits (amplifier 20, analogue-digital converter 21, buffer 22) for acquisition of signals representing the electrical activity of the brain, a processor 23 being used for acquisition and processing of these signals and an alert circuit 24 for the patient or for his environment, for example a light.

Expected Results in Epilepsy and Clinical Implications

It has been observed that some pairs of electrodes in the periphery of the epileptogenic zone systematically show a significant modification of their degree of synchronism before a seizure, particularly for example in the alpha (8-12 Hz), beta (15-30 Hz) and gamma (30-70 Hz) frequency bands. Interestingly, this synchronisations have recently been given considerable attention for their possible role in large scale integration phenomena during cognition. These results thus suggest that neuron populations subjacent to the epileptogenic zone modify their relations with larger scale variations before the seizure. These changes in synchronisations may cause "dynamic isolation" of the focus and could recurrently provide a neuron population that can easily be recruited by epileptic processes.

New analyses techniques for synchronisations of electroencephalography used in the method according to the invention can be used to very precisely quantify the pre-critical cerebral activity. This possibility of anticipating the occurrence of seizures opens up very broad medical prospects:
- in fundamental research, by characterisation of neurobiological modifications that occur during this precritical phase;
- clinically, by the possibility of warning the patient, and attempting to stop the initiating seizure by a therapeutic action.

In particular, electric neurostimulation recently appeared as a promising therapeutic solution for other pathologies, particularly for Parkinson's disease. In this context, the mechanical destruction of a predefined cerebral region has been replaced by the principle of a protective treatment by electric stimulations to reinforce or inhibit a neuron activity. In this respect, the possibility of anticipating seizures using the method according to the invention is decisive since it provides a solution to the question of "when to stimulate?". These stimulations may be applied when a pre-ictal state is detected and are aimed at destabilizing epileptogenic processes before they become irreversible at the time of the seizure. This is the approach that is preferred in the long term for patients being investigated by intracerebral electrodes.

Furthermore, the analysis technique used for synchronisations of electroencephalography can enable developments of "cognitive" actions. Some patients describe their ability to interrupt their initiating seizure by carrying out specific cognitive activities or by motor activities. These phenomena are probably based on destabilisation of the epileptic process by the appearance of new electrical activities within the cerebral cortex. Inventors have also demonstrated modulation of an epileptic activity by cognitive synchronisations.

Other actions could also be applied, for example pharmacological action consisting of administration of fast active antiepileptic drug (like benzodiazepines).

These possibilities of alert and actions available if seizures can be anticipated, necessarily require "real time" anticipation, in other words the results of mathematical calculations need to be obtained instantaneously in the method according to the invention, not later on.

The ability to anticipate seizures can also improve examinations performed during the pre-surgical check-up of partial pharmacoresistant epilepsies. In particular, the pre-critical cerebral scintigraph (SPECT-ictal) is facilitated if the team is alerted: injection of the radioactive tracer immediately before or at the beginning of the seizure improves the definition of the location of the epileptogenic centre. Hospitalisation times can then be considerably shortened and imaging system occupancy times can be optimised. The possibility of anticipating the occurrence of epilepsy seizures due to in depth and surface electroencephalography opens up a fairly broad range of prospects in social and clinical applications.

Mathematical Procedure Used for Calculating Phase Synchronism Between Two Signals The instantaneous phase of a signal may be calculated either using an analytic signal, a concept introduced by Gabor in 1946 and recently applied on experimental data, or by convolution with a complex specific wavelet (Lachaux et al, Human Brain Mapping, 1999).

For an arbitrary signal s(t), the analytic signal $\xi$ is a complex function dependent on time defined as follows:

$$\xi(t)=s(t)+j\tilde{s}(t)=A(t)e^{j\phi(t)} \quad (1)$$

where the function $\tilde{s}(t)$ is the Hilbert transform of s(t):

$$\tilde{s}(t) = \frac{1}{\pi} P.V. \int_{-\infty}^{+\infty} \frac{s(t)}{t-\tau} d\tau \quad (2)$$

P.V. states that the integral is calculated in terms of the Cauchy principal value. The instantaneous amplitude A(t) and the instantaneous phase $\phi(t)$ of the signal s(t) are only defined by equation (1). As can be seen in equation (2), $\tilde{s}(t)$ is considered to be the convolution product of s(t) and $1/\pi$. This means that the Hilbert transform is equivalent to a filter for which the amplitude response is unitary and the phase response is offset by $\pi/2$ for all frequencies. Although this transform can be applied in theory to signals with a wide frequency band, the phase concept is not very clear in this case. In practice, only narrow band signals obtained by filtering are used. Consequently, filtering is always done in a specific frequency band. Several frequency bands may be selected. The same frequency band is used for two signals in case of 1:1 synchronism. Different frequency bands are used for the study of n:m synchronisms. The statistical level of PLS synchronisation between two signals is evaluated using one of the following two indexes:

the circular variance of the phase difference ($\Delta\phi$) between signals; or the Shannon normalised entropy of this phase difference ($\Delta\phi$).

The circular variance is such that:

$$VC = \left| \sum_{k=1}^{M} e^{i\Delta\phi k} \right|$$

Shannon's normalised entropy is such that:

$$\gamma=(H_{max}-H)/H_{max}$$

where the entropy H is defined by:

$$H = \sum_{k=1}^{N} p_k \ln p_k$$

where N is the number of classes, $H_{max}=\ln(N)$ is the maximum entropy, and $p_k$ is the relative frequency of the phase difference in the $k^{th}$ class. The optimum number of classes is $N=\exp[0.626+0.4\ln(M-1)]$ where M is the number of elements (phase difference) to be sorted. With this normalisation, the values of $\gamma$ for 95% of "surrogates" (replacement values) are included between 0 (uniform distribution and no synchronisation) and 1 (perfect synchronisation). This calculation is made for all pairs of sensors recorded in the assembly protocol. The number of distinct pairs for the 27 electrodes in a standard assembly is 26×25/2=325, and the number for 128 electrodes is 8001.

Figure 4:
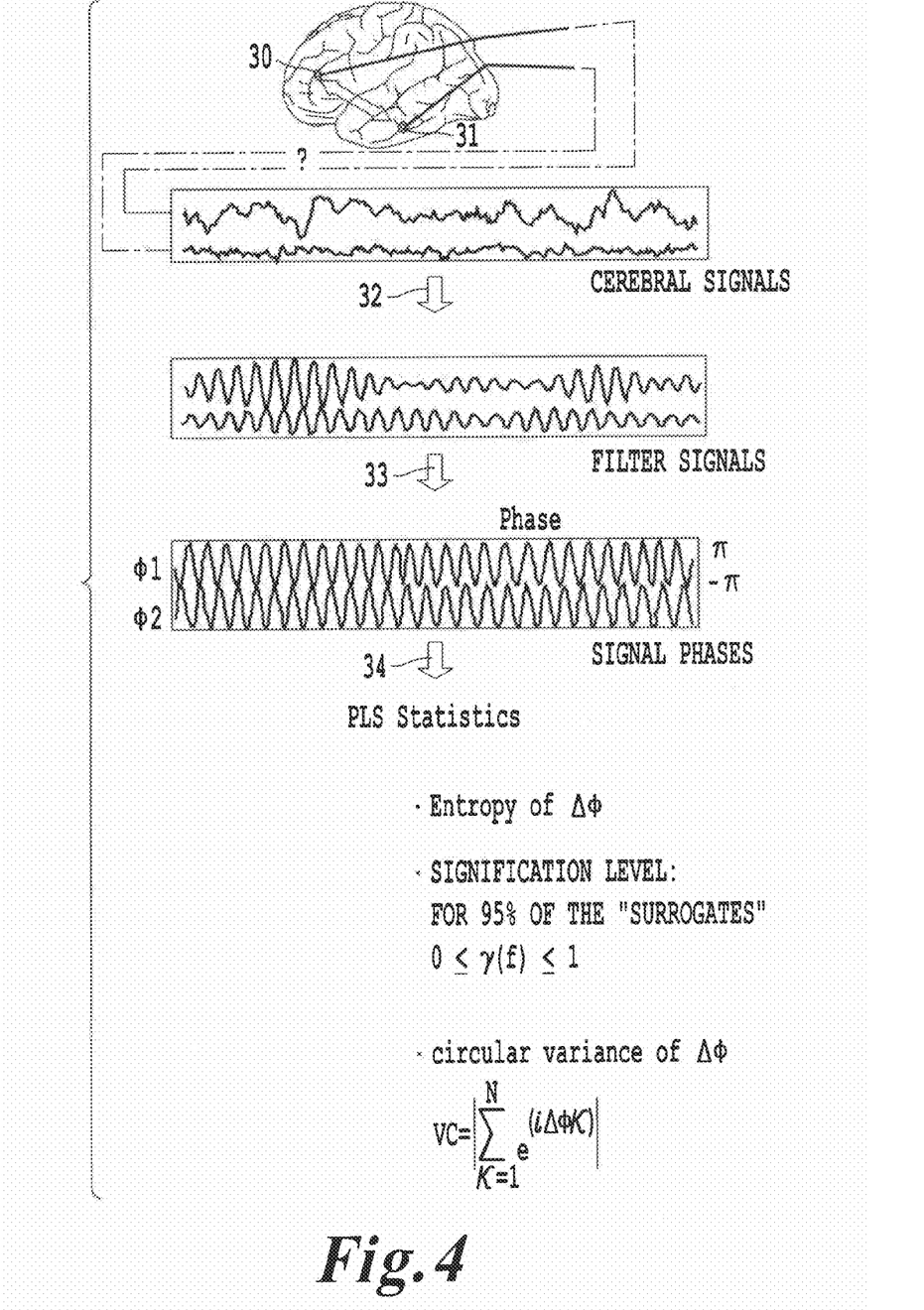
FIG. 4 illustrates explanatory chronograms showing the treatment of electroencephalograms using the method according to the invention.
Figure 5:
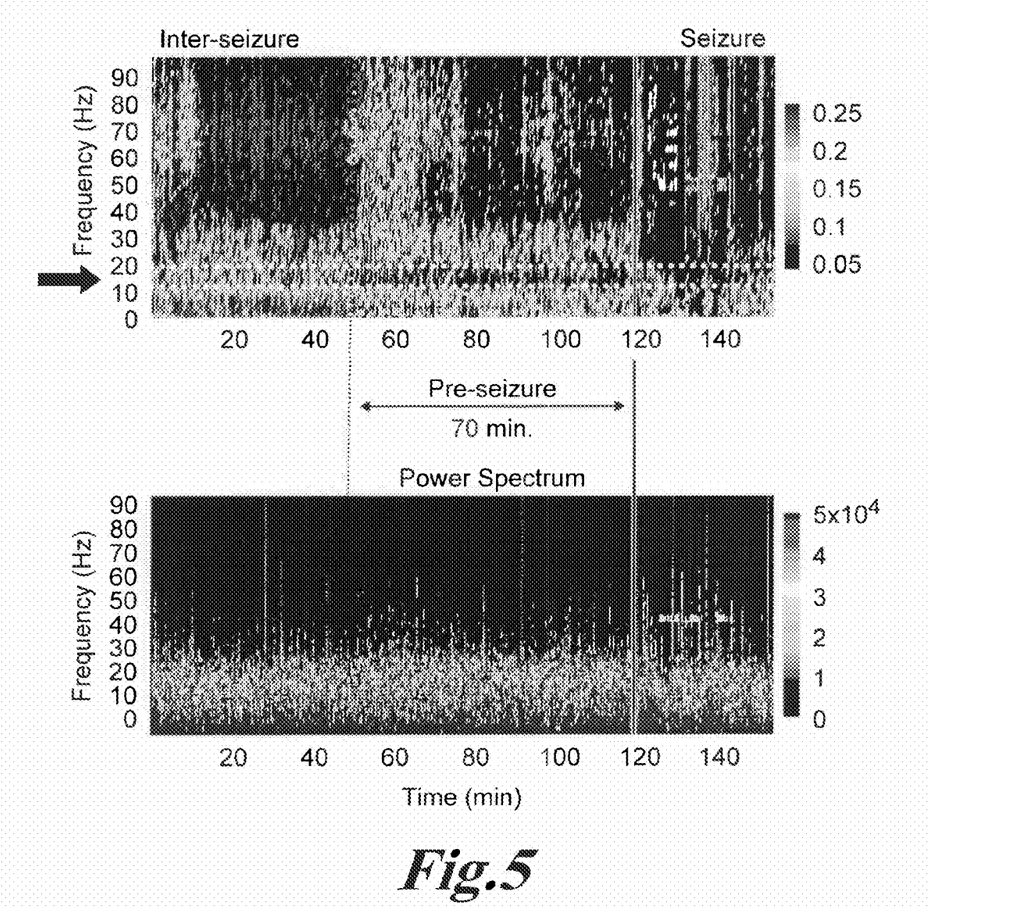
FIG. 5 illustrates an example embodiment of the method for real time treatment of epilepsy according to the invention.

Thus, as illustrated in FIG. 4, we have the following in sequence:

passband filtering of two signals obtained with two electrodes 30 and 31 (f±1 Hz);

Hilbert's transform of these signals;

evaluation of the statistical level of the PLS synchronisation using two indexes:

entropy of $\Delta\phi$ (phase difference between $\phi 1$ and $\phi 2$);

circular variance of $\Delta\phi$.

The second step consists of setting up the database of calibrated states of the patient as a function of the objective to be achieved.

The third step is a discrimination step for decision-making purposes. Considering a recording period equal to 10 seconds in pathology, but sometimes much shorter for the discrimination of cognitive states for which quantification by the synchronisation method is known, an attempt is made to assign it to a class characterising one cerebral state among several. This is a sort problem, which assumes that a set of classes has been defined in advance. The main difficulty is the dimension of the variables space. Quantifying synchronisation between all pairs of sensors in six frequency bands requires a variables space with dimension p=1950 (325×6) for a setup with 27 electrodes. The expression for the a posteriori probability of the analysed time window x belonging to the k different groups of cerebral states is as follows (Bayes's theorem):

$$P(G_r/x) = P(G_r) \cdot P(x/G_r) \Big/ \sum_{j=1}^{K} P(Gj) \cdot P(x/Gj) \text{ where}$$

$$r = 1, \ldots, k$$

where $P(G_r)$ is the a priori probability of belonging to a class and in practice is estimated by the frequency of elements of $G_r$ in the total sample. The different values $P(x/G_r)$ are estimated by probability densities. For each new analysed period x to be sorted into one of the k groups, a search is made for the q closest neighbours of each of the k groups, thus defining the average radius $r_k$ of the hypersphere $HS(r_k,x)$ containing the average of the q neighbbours of x and the volume $A_k$ of the corresponding hypersphere in the space $R^p$. Thus, the probability density P(x/Gr) can be estimated as follows:

$$\hat{P}(x/G_r) = \frac{q}{n_r A_r}$$

and x is assigned to the group j∈[1,k] if: P(Gj/x)=max{P (Gr/x); r=1, 2, . . . , k}.

EXAMPLE USE OF THE INVENTION

The device according to the invention was applied to electrical intracranian cerebral recordings of patients being subjected to surgical treatment of their temporal epilepsy and it has thus been demonstrated that seizures can be anticipated by several minutes and there is a deterministic "road towards seizure" phenomenon, as illustrated in FIG. 4. The device according to the invention enables the seizure in the 10-20 Hz frequency band to be anticipated almost 20 minutes before the seizure, and is characterised by reduced synchronisation. The power spectrum, a classical signal processing procedure, does not give such clear modifications.

The method according to the invention is particularly suitable for clinical situations and makes it possible to extend the results to surface electroencephalography, due to its low sensitivity to recording artefacts.

REFERENCES

[1] LE VAN QUYEN M., MARTINERIE J., NAVARRO V., BOON P., D'HAVE M., ADAM C., RENAULT B., VARELA F. AND BAULAC M., "Anticipation of epileptic seizures from standard surface EEG recording" (2001, The Lancet, 357, pages 183-188).

[2] MARTINERIE J., ADAM C., LE VAN QUYEN M., BAULAC M., CLEMENCEAU S., RENAULT B., VARELA F., "Can epileptic seizure be anticipated by non-linear analysis?" (Nature Medicine 1998, vol. 4, 10, pages 1173-1176).

[3] VARELA F., LACHAUX J. P., RODRIGUEZ E., and MARTINERIE J., "The Brainweb: Phase synchronisation and Large-scale integration" (Nature Reviews Neuroscience 2001, 2, pages 229-239).

The invention claimed is:

1. A method of a real time medical or cognitive monitoring device for analyzing synchronizations of electroencephalography of an individual using a set of sensors starting from cerebral electromagnetic analysis of the individual, comprising:
    creating a database comprising:
        acquisition and digitization of electrophysiological signals output from the sensors,
        calculating a correlation of phase variations between all pairs of sensors recorded in an assembly protocol, in frequency bands between 0 and 2000 Hz, to build up the database of classes each characterizing a reference state of cerebral electromagnetic activity of said individual;
    statistical validation, by the real time medical or cognitive monitoring device, of a period analyzed in real time, which assigns the period to a class in the database; and
    detecting, by the real time medical or cognitive monitoring device, a specific period with a determined degree of synchronization.

2. A method according to claim 1, further comprising an analysis associated with at least one type of electrophysiological signals among electrocardiograms, electrooculograms, electrodermograms, breathing signals.

3. A method according to claim 1, wherein a PLS method is used during the statistical validation, which estimates a phase difference between oscillations of signals from two electrodes.

4. A method according to claim 3, wherein a statistical level of PLS synchronization between two signals is evaluated using circular variance of the phase difference between the signals.

5. A method according to claim 3, wherein a statistical level of PLS synchronization between two signals is evaluated using normalized Shannon entropy of the phase difference between the signals.

6. Application of the method according to claim 1, to real time medical or cognitive monitoring.

7. Application of the method according to claim 1, for characterizing and differentiating physiological or pathological states.

8. Application of the method according to claim 7, for anticipating occurrence of epileptic seizures.

9. Application of the method according to claim 7, for diagnosis assistance in early stage of Parkinson's and Alzheimer's diseases.

10. Application of the method according to claim 7, for diagnosis assistance of schizophrenia and depression.

11. A real time medical or cognitive monitoring device starting from cerebral electromagnetic analysis of an individual, comprising:
    means for acquiring and digitizing electrophysiological signals output from sensors;
    means for calculating correlation of phase variations between all pairs of sensors recorded in an assembly process, in frequency bands between 0 and 2000 Hz, to build up a database of classes each characterizing a reference state of cerebral electromagnetic activity of said individual;
    means for statistically validating a period analyzed in real time to assign the period to a class in the database;
    means for detecting a cognitive period or a specific pathological period; and
    means for sending an alert signal if applicable.

12. A device according to claim 11, further comprising means for performing an analysis associated with at least one type of electrophysiological signals among electrocardiograms, electrooculograms, electrodermograms, breathing signals.

13. A device according to claim 11, wherein a PLS method is used by the means for statistically validating, which estimates a phase difference between oscillations of signals from two electrodes.

14. A device according to claim 13, wherein a statistical level of a PLS synchronization between two signals is evaluated using circular variance of the phase difference between the signals.

15. A device according to claim 13, wherein a statistical level of PLS synchronization between two signals is evaluated using normalized Shannon entropy of the phase difference between the signals.

16. A device according to claim 11, further comprising:
    circuits for acquisition of signals representing electrical activity of the brain;
    a processor configured for acquisition and processing of the signals; and
    an alert circuit for the patient or for his/her environment.

17. A device according to claim 11, which is a device that the individual can carry himself or herself.

18. A device according to claim 11, miniaturized to be implanted subcutaneously.

* * * * *